United States Patent [19]  [11] Patent Number: 4,646,740
Peters et al.  [45] Date of Patent: Mar. 3, 1987

[54] AUTOMATIC HEMOCLIP APPLIER

[75] Inventors: Rudolph Peters; Ronald L. Peters; William Taylor, all of Oakland, Calif.

[73] Assignee: Edward Weck & Co., Inc., Research Triangle Park, N.C.

[21] Appl. No.: 237,465

[22] Filed: Feb. 23, 1981

[51] Int. Cl.4 .......................................... A61B 17/12
[52] U.S. Cl. ................... 128/325; 227/DIG. 1
[58] Field of Search ............ 128/325, 334 R, 337; 227/DIG. 1, 19; 29/243.56; 221/312 B; 30/40.2

[56] References Cited

U.S. PATENT DOCUMENTS

| | | | |
|---|---|---|---|
| 2,733,441 | 2/1956 | White | 227/DIG. 1 B X |
| 3,098,232 | 7/1963 | Brown | 227/DIG. 1 B X |
| 3,954,108 | 5/1976 | Davis | 128/325 |
| 3,955,581 | 5/1976 | Spasiano et al. | 128/334 R |
| 4,086,926 | 5/1978 | Green et al. | 128/334 R |
| 4,226,242 | 10/1980 | Jarvik | 227/DIG. 1 B X |
| 4,296,751 | 10/1981 | Blake et al. | 227/DIG. 1 X |
| 4,325,376 | 4/1982 | Klieman et al. | 128/325 |

Primary Examiner—Michael H. Thaler
Attorney, Agent, or Firm—Harris Zimmerman; Howard Cohen

[57] ABSTRACT

A device for applying a plurality of hemoclips to blood vessels and the like includes a longitudinally disposed frame having a pistol grip and an opposed trigger lever extending from the proximal end thereof. A narrow, internal passageway extends the length of the frame, from a loading opening at the proximal end to a fixed lower jaw at the distal end of the frame. A plurality of U-shaped hemoclips is disposed in the passageway with the points thereof extending toward the distal jaw portion. An upper jaw extends from a clevis member which straddles the frame and is pivotally joined to an upper medial portion thereof. The trigger lever is pivotable to cause the clevis member to pivot upwardly and the upper jaw to close upon the lower jaw to crush a hemoclip disposed therebetween. A piston resiliently biased in the internal passageway urges the hemoclips toward the jaw portion, and a feed release lever is disposed at the proximal end of the passageway to discharge a hemoclip from the passageway to the jaw portion with each full actuation of the upper jaw.

28 Claims, 23 Drawing Figures

FIG_8  FIG_9

FIG_10  FIG_11

FIG_12  FIG_13

AUTOMATIC HEMOCLIP APPLIER

BACKGROUND OF THE INVENTION

A hemostatic clip, or hemoclip, comprises a generally V-shaped metal member which is designed to receive a blood vessel within the concave portion thereof. The hemoclip is adapted to be flattened by a special tool so that the opposed legs thereof are brought together as closely as possible to squeeze the blood vessel therebetween and block blood flow therethrough. Hemoclips have gained wide acceptance in the medical field, particularly for use in surgical procedures and in emergency treatment procedures. The reason for this widespread acceptance is the rapidity with which hemoclips can be applied to shut off bleeding blood vessels at a surgical site or at the site of trauma due to accident.

However, a major drawback in the use of hemoclips is the special tools known in the prior art which are adapted for applying the hemoclips. Many of these tools are merely pliers having special jaws adapted to engage a hemoclip. These devices require that the hemoclips be applied one at a time, and that the tool be resupplied with a fresh hemoclip after a dispensing procedure is finished. There is obviously a great amount of time which is wasted in applying the hemoclips one at a time, and this time may be very critical to a patient undergoing treatment or surgery.

Other devices known in the prior art for applying hemoclips are capable of substantially flattening a hemoclip about a blood vessel, yet are incapable of completely flattening the hemoclip to completely shut off the blood flow in the vessel. This fault may be linked to designs based on the concept of disposability, and the concommitant requirement of cheap materials which lack the strength and rigidity required to apply a hemoclip properly.

SUMMARY OF THE PRESENT INVENTION

The present invention generally comprises a device for storing, dispensing, and applying a plurality of hemostatic clips to blood vesssels or the like. The most salient features of the invention are its ability to store a large number of hemoclips, its ability to dispense and apply the hemoclips in rapid sequence, its ability to crimp completely the legs of the hemoclip to effect total occlusion of a blood vessel, and its ability to be sterilized and re-used many times. The device also includes a magazine-type reloading assembly which facilitates rapid reloading of the device.

The device of the present invention includes a longitudinally extending frame having a pistol grip and an opposed trigger lever extending from the proximal end of the frame. The distal end of the frame includes a fixed lower jaw and a moveable upper jaw which are adapted to crimp together the opposed legs of a V-shaped hemoclip. The upper jaw is secured to a clevis member which straddles the upper medial portion of the frame and is pivotally secured thereto. The proximal end of the clevis member is engaged by a roller which is pivotally supported on the distal end of the trigger lever. The trigger itself is adapted to undergo a compound movement consisting of an initial translation toward the proximal end of the frame when the trigger is first squeezed toward the handle, followed by a pivoting motion in which the roller at the distal end of the trigger lever engages the proximal end of the clevis member to rotate the upper jaw downwardly into impingement with the lower jaw.

An enclosed feed path for storing and dispensing the plurality of hemoclips extends the length of the frame, and includes a longitudinal passageway having a narrow rectangular cross-sectional configuration. One narrow side of the passageway is defined by a sinusoidal leaf spring. The plurality of hemoclips is disposed in column fashion in the passageway with the pointed ends thereof extending toward the distal end of the frame, with like legs of the hemoclips impinging upon the sinusoidal leaf spring. A spring biased piston rod impinges upon the proximal-most hemoclip and urges the column of hemoclips toward the distal end of the frame in closely spaced relationship. The sinusoidal spring at one edge of the passageway prevents the pointed ends of the hemoclips from binding as they translate along the passageway under the resilient urging of the piston rod.

A hemoclip releasing member includes a rod disposed translatably in a track formed in the exterior of the frame and extending parallel to the interior passageway. The proximal end of the clip releasing member is secured to the trigger lever for translation thereby, while the distal end of the clip releasing member includes a stop dog which extends into a window in the distal-most portion of the interior passageway in the frame. A button extends outwardly from the clip releasing member, and is engageable by a notch in the clevis member which supports the upper jaw. As the upper jaw descends to crimp a hemoclip, the button is urged outwardly by the notch in the clevis member, so that the stop dog is urged out of the window in the passageway to permit a single hemoclip to advance to the end of the passageway. The hemoclip is halted by the upper jaw which blocks the distal end of the passageway when it descends. When the trigger is released and the upper jaw returns to its fully open, quiescent position, the stop dog returns to its blocking position within the window at the distal end of the passageway. The stop dog translates forward as the trigger is released to urge the dispensed hemoclip distally into opposed grooves in the upper and lower jaw. The hemoclip is thus advanced and positioned to be applied by the next actuation of the trigger lever. Thus every operation of the device applies one hemoclip while dispensing and preparing another hemoclip for subsequent application.

DESCRIPTION OF THE PREFERRED EMBODIMENT

Figures 1, 2:
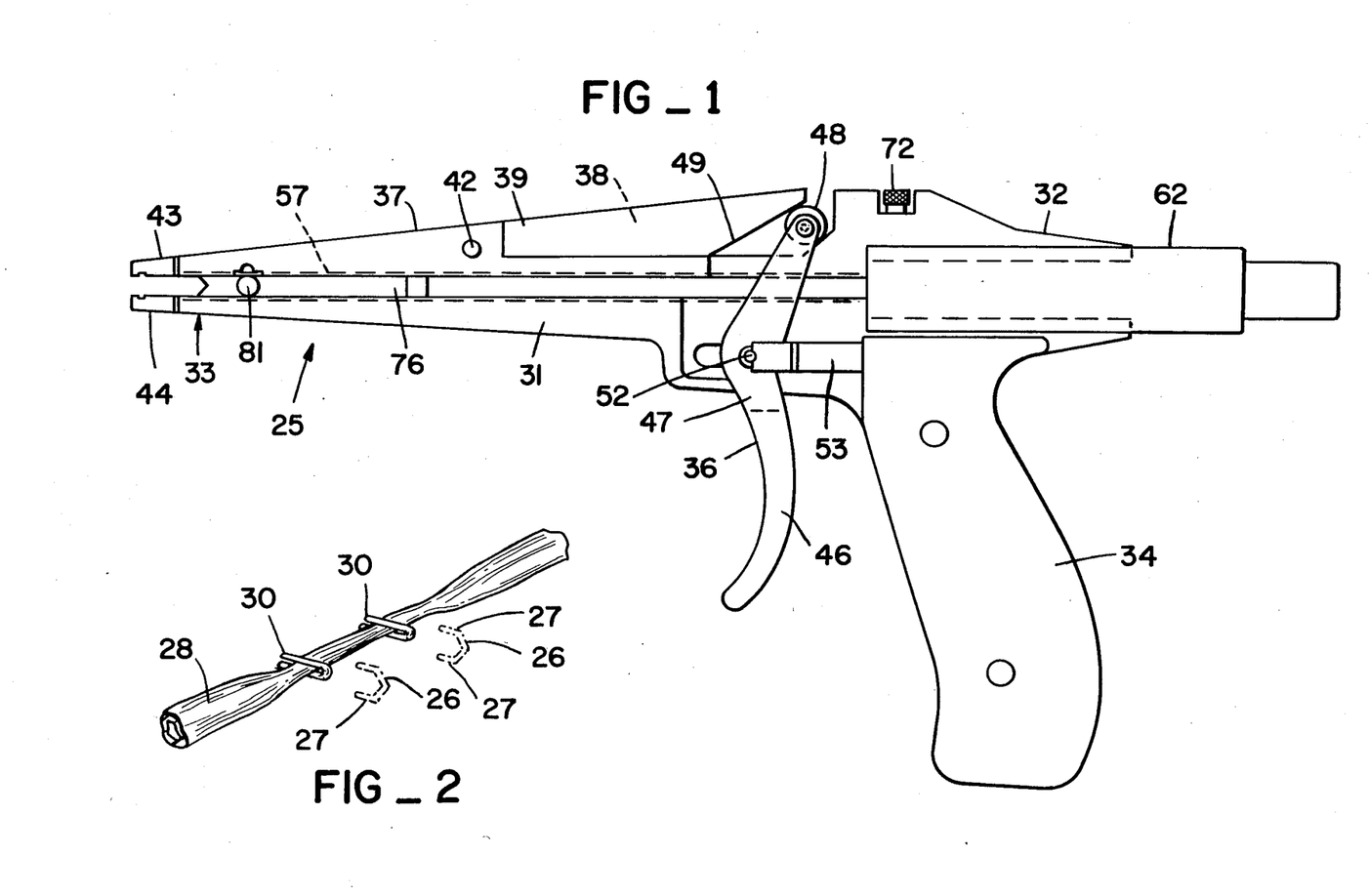
FIG. 1 is a plan view of the hemoclip applying device of the present invention.
FIG. 2 is a perspective view of a typical hemoclip application.

With reference to FIG. 1, the preferred embodiment of the present invention generally comprises a pistol-like device 25 for storing a plurality of hemostatic clips, and for dispensing and applying the hemostatic clips singularly and sequentially. As shown in FIG. 2, the hemostatic clips 30 referred to herein generally comprise a V-shaped base portion 26 and a pair of leg members 27 extending distally from the base portion. The base portion and the leg members define an opening 50 which is adapted to receive a blood vessel 28 or the like. Hemostatic clips are formed of a rather stiff, form-retaining metal wire or the like, and are adapted to be deformed by crimping to bring the leg members 27 as closely adjacent as possible and in generally parallel relationship. As shown in FIG. 2, the crimped hemostatic clips will collapse the walls of the blood vessel 28 and prevent fluid flow therethrough. Such hemostatic clips are known in the prior art, and are in common usage for medial and surgical procedures.

Figure 3:
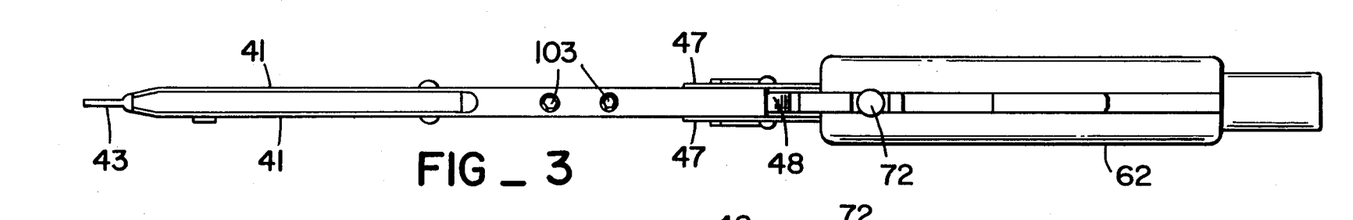
FIG. 3 is a top view of the hemoclip applying device of the present invention.
Figure 4:
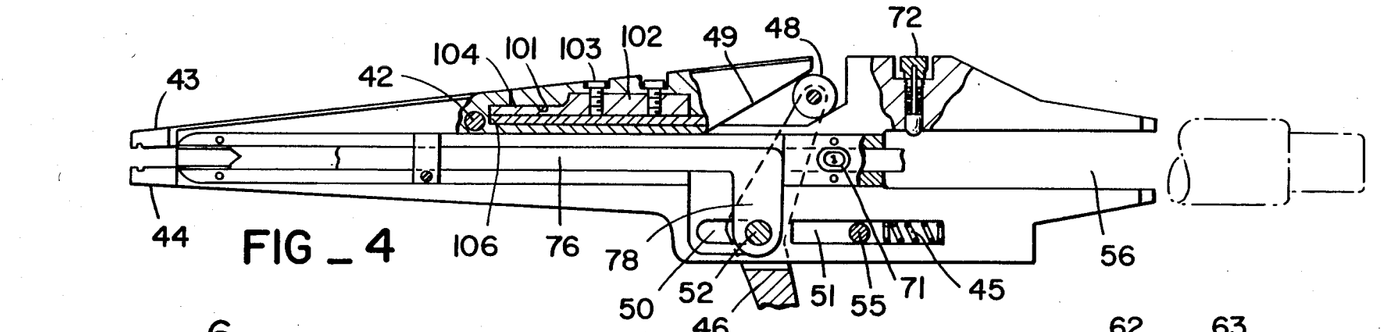
FIG. 4 is a partially cut-away side view of the device shown in FIGS. 1 and 3.
Figure 5:
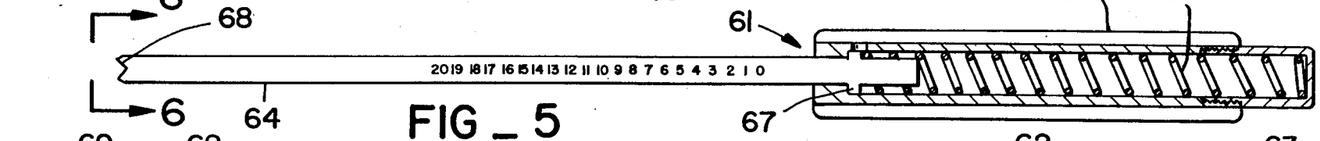
FIG. 5 is a side elevation of the hemoclip advancing mechanism of the present invention, shown in the extended position.
Figure 6:
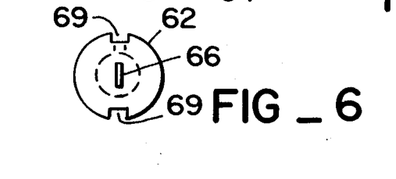
FIG. 6 is an end view of the hemoclip advancing apparatus shown in FIG. 5.

With references to FIGS. 1, 3, and 4, the device 25 comprises a frame member 31 which extends longitudinally from a proximal end 32 to a distal end 33. As shown in FIG. 3, the lateral width of the frame 31 is much smaller than the longitudinal extent thereof. A handle portion 34 extends downwardly from the proximal end of the frame in the fashion of a pistol grip. A trigger assembly 36 extends generally parallel to and distally of the handle portion 34. The trigger assembly 36 is disposed to be engaged by the index finger and second finger of the hand (left or right) grasping the handle 34.

It may be noted that the upper edge 37 of the frame 31 extends obliquely upwardly from the distal end 33 toward the medial portion of the frame. A longitudinally extending, slot-like cutout 38 extends concavely into the upper edge 37 of the frame, and includes a notch 106 extending distally therefrom. An upper jaw assembly 39 includes a clevis portion 41 which straddles the distal upper portion of the frame and is pivotally secured thereto by a pivot pin 42. Extending distally and longitudinally from the clevis portion 41 is an upper jaw 43. The upper jaw 43 is in closely adjacent opposition to a lower jaw 44 which extends distally and fixedly from the frame 31. It may be appreciated that counter-clockwise rotation of the clevis member 41 about the pivot 42 will cause the upper jaw 43 to advance toward and impinge upon the lower jaw 44.

The upper jaw assembly 39 also includes a longitudinally extending slot 101 formed therein and adapted to receive a block 102. The block is secured in the narrow slot by a pair of screws 103 which are received in tapped holes therein. An arm spring 104 extends distally from the block 102, the distal end of the arm spring being engaged in the notch 106. Rotation of the upper jaw assembly in a counter-clockwise direction causes flexure of the arm spring 104, the restoring force of which acts to return the jaw assembly it its quiescent position shown in FIGS. 1 and 4.

The means for rotating the upper jaw portion and clevis portion of the device is the trigger assembly 36. The trigger lever 46 extends downwardly from a clevis portion 47 which straddles the lower medial portion of the frame 31. A roller 48 is rotatably secured between the upper ends of the clevis member 47, the roller 48 being disposed in the slot 38 and impinging upon the proximal oblique surface 49 of the upper jaw assembly 39.

With reference to FIG. 4, a slot 51 is disposed in the lower medial portion of the frame, extending parallel to the longitudinal axis of the frame. Another slot 50 is disposed in the lower medial portion of the frame distally of the slot 51 and generally aligned therewith. A pin 52 extends freely through the slot 50, and also through both sides of the clevis portion 47. With reference to FIG. 1, a longitudinally bifurcated slide member 53 is translatably secured in the slot 51, and is joined by a screw 55 extending freely through the slot 51 and received in both sides thereof. A compression spring 45 disposed at the proximal end of the slot 51 impinges on the screw 55 and biases the slide member 53 to translate toward the distal end of the device. This resilient force tends to oppose the actuation of the trigger assembly by the well-known motion of squeezing the trigger and urging it toward the handle 34.

It may be appreciated that actuation of the trigger mechanism produces a complex motion of the trigger assembly. Initial squeezing of the trigger toward the handle causes the slide 53 to translate toward the proximal end of the slot 51. After full translation of the slide member 53, when the pin 52 abuts the proximal end of the slot 50, further squeezing of the trigger will cause it to pivot about the pin 52 in a counter-clockwise direction (FIGS. 1 and 4). The rotation about the pivot 52 causes the roller 48 to translate toward the distal end of the device and traverse the oblique surface 49 of the upper jaw assembly. This action causes the upper jaw assembly to pivot in the counterclockwise direction about the pin 42, so that the upper jaw 43 closes upon the lower, fixed jaw 44. The relatively large distance between the pivot 42 and the oblique surface 49, together with the relatively large angular excursion of the trigger compared to the jaw, provides a large mechanical advantage in the closure of the jaws 43 and 44.

Figure 19:
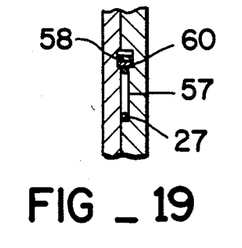
FIG. 19 is a partial cross-sectional elevation of the device, showing the internal passageway for storing and dispensing hemoclips.
Figure 20:
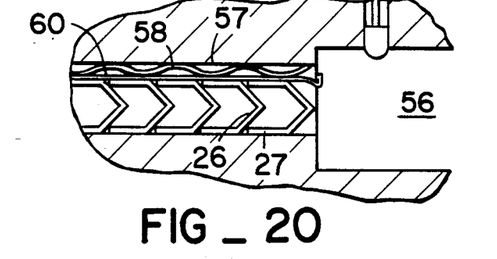
FIG. 20 is an enlarged cut-away view of a portion of the internal passageway of the invention.

With continued reference to FIGS. 1 and 4, a slot 56 extends deeply into the proximal end of the frame and is disposed coaxially with the longitudinal axis thereof. An interior passageway 57, shown also in FIGS. 19 and 20, extends the length of the frame member from the distal end of the slot 56 to the distal end 33 of the frame. The interior passageway is provided with a narrow rectangular cross-section, the upper side of the cross-sectional configuration being defined by a movable blade wall 60 backed by a leaf spring 58 formed as a smooth, periodic curve. The passageway 57, which comprises an enclosed channel, is dimensioned to receive a plurality of hemostatic clips 30 with the pointed legs 27 thereof pointing toward the distal end of the passageway and abutting the V section 26 of the adjacent hemostatic clip. In the preferred embodiment of the present invention, at least twenty hemostatic clips can be stored along the full length of the passageway 57. The proximal end of the blade wall 60 is formed as a lip extending into the passageway to prevent loss of the clips therein during loading procedures.

Figure 7:
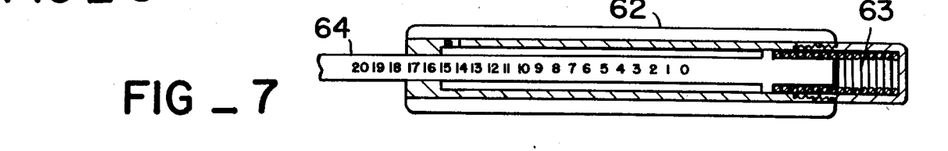
FIG. 7 is a partial side elevation of the hemoclip advancing apparatus, shown in the retracted position.

The present invention also includes a spring plunger assembly 61, as shown in FIGS. 3-7. The assembly 61 includes a hollow cylindrical member 62 which is closed at its proximal end to retain therein a helical compression spring 63. A plunger 64 extends outwardly from the tubular member 62 through a slot opening 66 (FIG. 6) disposed generally co-axially with the tubular member 62. The plunger 64 includes an internal stop lug 67 which limits the outward translation of the plunger. The distal end of the plunger is provided with a V-shaped notch 68 which is adapted to engage the V-shaped base portion 26 of a hemostatic clip. The distal vertices of the notch 68 are bevelled to prevent interference with the lip at the proximal end of the blade wall 60. The cylindrical member 62 includes a pair of diametrically opposed, longitudinally extending grooves which are adapted to engage the opposed sides of the slot 56 of the frame member. The plunger 64 is provided with serial numerical indicia spaced consecutively along a medial portion thereof. It may be appreciated that the plunger 64 is adapted to be received within the closed passageway 57 of the frame member, with the tubular member 62 received in the slot 56 of the frame. Assuming that the passageway 57 is initially filled with hemostatic clips in abutting relationship, the plunger 64 is substantially retracted within the tubular member 62, compressing the spring 63 in the proximal end of the tubular member, as shown in FIG. 7. The expansion force of the spring 63 urges the plunger toward the distal end of the passageway 57, maintaining the hemostatic clips in abutting relationship within the passageway. It may be appreciated that the movable blade wall 60 yields toward the smoothly curving spring 58 under slight pressure to prevent the pointed ends of the hemostatic clips from sticking and binding within the passageway. A display window 71 extends from a medial external portion of the frame to intersect with the passageway 57. The window 71 displays the serial numerical indicia which are formed on the plunger 64. As hemostatic clips are dispensed from the distal end 33 of the device, the plunger advances incrementally toward the distal end of the passageway 57, and the serial numerical indicia passes decrementally past the display window 71. The indicia on the plunger 64 are positioned so that the number displayed in the window 71 corresponds to the number of hemostatic clips remaining within the passageway 57. A detent screw assembly 72 is disposed in the upper medial portion of the frame member, and is adapted to retain the spring plunger assembly 61 in its operative relationship with the frame.

At the distal end of the frame, the passageway 57 extends to an opens to the fixed lower jaw 44 and rotatable upper jaw 43. Each of the jaws 43 and 44 is provided with a longitudinally extending groove 73. With the upper jaw in the fully open position, the two grooves 73 are aligned directly with the upper and lower extents of the inner passageway 57. The grooves 73 are adapted to receive the leg portions 27 of a hemostatic clip, as shown, for example, in FIG. 8.

The distal-most end of the passageway 57 is provided with a cutout, or window, 74 formed in the side wall of the passageway 57. A longitudinally extending track 77 is formed in the outer side surface of the frame, extending from the distal-most portion thereof to the medial portion thereof adjacent to the trigger assembly and disposed parallel to the internal passageway 57. Received in the track 77 is a slide member 76 which is adapted for longitudinal translation along the track. The proximal end of the slide member 76 is provided with an arm 78 extending perpendicularly therefrom and joined to the trigger assembly by the pin 52 extending therethrough. It may be appreciated that the slide member 76 is caused to translate reciprocally in the track 77 by actuation of the trigger assembly, as described in the foregoing.

With particular reference to FIGS. 8-11, the distal end of the member 76 is provided with a V-shaped notch 78A which is configured to engage the V portion 26 of a hemostatic clip. Directly adjacent to the notch 78A is a shoulder 79 which has the same V configuration as the notch 78A, and which extends laterally inwardly through the window 74 and into the passageway 57. As the column of hemostatic clips advances through the passageway 57 to the distal end thereof, the shoulder 79 acts as a stop to limit translation of the clips.

Figures 12, 13:
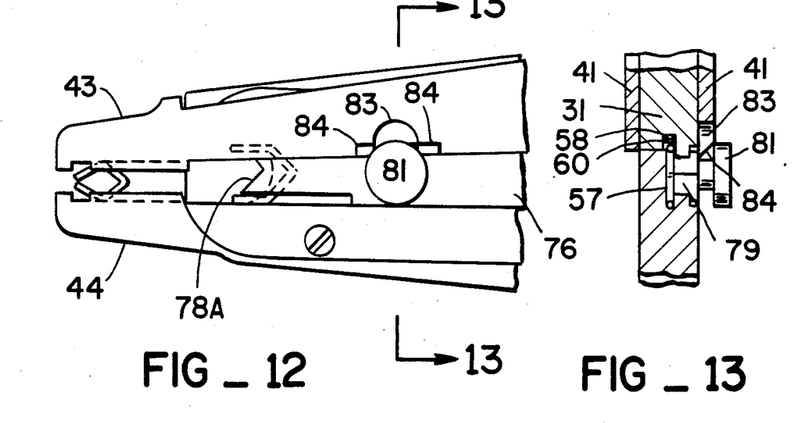
FIG. 12 is a partial side elevation of the jaw portion of the invention, showing the upper jaw descending to crimp and flatten a hemoclip while another hemoclip is advanced toward the jaws.
FIG. 13 is a cross-sectional elevation of the device, taken along line 13—13 of FIG. 12.

Extending laterally outwardly from the member 76 is a clip release button 81. The button 81 extends from a short shank 82 which projects outwardly from the member 76. The upper jaw assembly 39 is provided with a semi-circular notch 83 formed in the lower edge of the clevis member 41 which is disposed on the same side of the device as the button 81. The notch 83 is flanked on either side by a pair of oblique camming surfaces 84 which extend downwardly and inwardly in the same edge of the clevis member 41. The notch 83 is slightly larger in diameter than the shank 82 so that the latter may be received in the former. The camming surfaces 84 are adapted to impinge upon the inner surface of the button 81, as shown in FIGS. 12 and 13, so that the button and the member 76 are urged laterally outwardly by the camming surfaces 84 during closure of the upper jaw assembly. The lateral outward movement of the member 76 causes the shoulder 79 at the end thereof to move out of its blocking position in the window 74 of the passageway 57, so that a hemostatic clip may be released by the shoulder 79 and permitted to advance to the distal end of the passageway 57.

Figure 8:
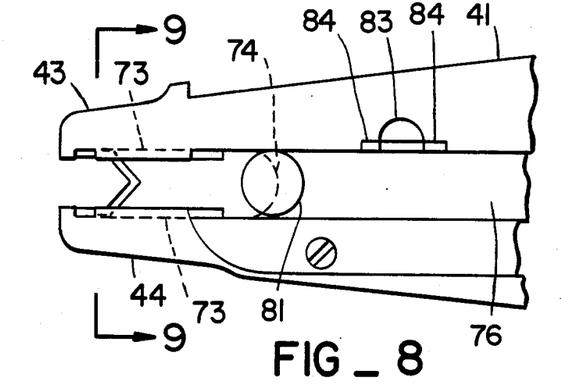
FIG. 8 is a partial side elevation showing the jaw portion of the invention at the beginning of a dispensing procedure.
Figure 9:
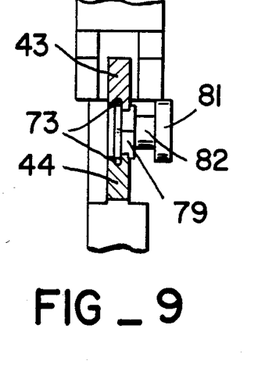
FIG. 9 is a cross-sectional view of the jaw portion of the invention, taken along lines 9—9 of FIG. 8.
Figure 10:
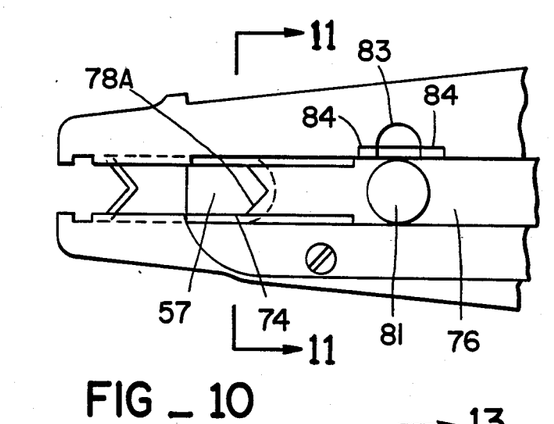
FIG. 10 is a partial side elevation of the jaw portion of the invention, shown after initiation of a dispensing sequence.
Figure 11:
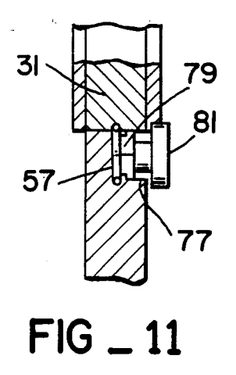
FIG. 11 is a cross-sectional view of the jaw portion of the invention, taken along line 11—11 of FIG. 10.

The sequence of operation of the preferred embodiment may best be understood with reference to FIGS. 8-18 taken in sequence. As shown in FIGS. 8 and 9, the device 25 is initially in its quiescent disposition with the trigger assembly fully released, the slide member 76 extending fully forwardly between the jaws 43 and 44, and a hemostatic clip lodged in the grooves 73 of the upper and lower jaws 43 and 44. It may be appreciated that in this disposition the button 81 is longitudinally offset from the notch 83 and the camming surfaces 84. Also, the movable jaw 43 is fully open. Initial adduction of the trigger lever 46 against the spring force of the spring 45 causes an initial translation of the trigger assembly toward the proximal end of the device. As a result, the members 53 and 76, which are joined to the trigger assembly by the pin 52, are caused to translate in concert with the trigger assembly. The shoulder 79 in the window 74 pushes the column of hemostatic clip proximally against the spring force of the spring 63 as the end 78 moves proximally to clear the jaws. At full translation of the trigger assembly, the button 81 is brought into registration with the notch 83, as shown in FIG. 10, and the member 76 is completely retracted from its quiescent position between the jaws.

After the trigger assembly has translated to its limit, further squeezing of the trigger lever 46 causes the trigger assembly to rotate about the pin 52. As described in the foregoing, this rotation causes the roller 48 to traverse the oblique surface 49 of the upper jaw assembly, and to rotate thereby the upper jaw assembly about the pin 42 against the spring force of the spring arm 104. As a result, the upper jaw 43 begins to descend toward the lower jaw 44, as shown in FIGS. 12 and 13. The hemostatic clip which is lodged between the jaws 43 and 44 is caused to undergo initial crimping which brings the pointed ends thereof together and captures therebetween a blood vessel or the like.

Figure 14:
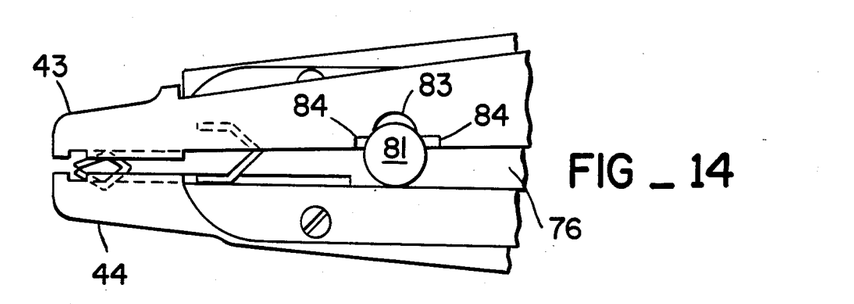
FIG. 14 is a partial side elevation of the jaw portion of the invention, shown with the jaws close to complete closure.
Figure 15:
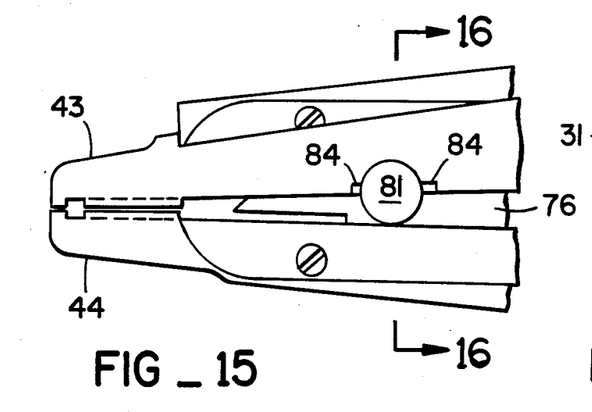
FIG. 15 is a side elevation of the jaw portion of the invention, showing the jaws thereof in the completely closed disposition.
Figure 16:
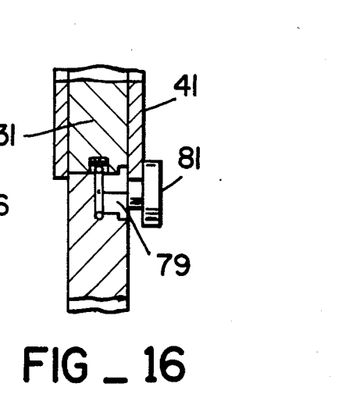
FIG. 16 is a cross-sectional elevation of the device, taken along line 16—16 of FIG. 15.

As the upper jaw assembly continues to descend, the camming surfaces 84 engage the inner surface of the button 81, driving the button laterally outwardly. When the jaw is substantially closed, as shown in FIG. 14, the member 76 is driven laterally outwardly a sufficient distance to remove the shoulder 79 from its blocking position in the window 74 of the passageway 57. At that point a single hemostatic clip is driven forwardly by the resilient pressure of the plunger 64 in the passageway 57. The single clip thus advances distally of the notch end 78 of the member 76. However, due to the substantially closed position of the upper jaw 73, the released hemostatic clip can advance only to the distal-most portion of the passageway 57. The released clip is thus prevented from interfering with the closing of the jaws as they effect total flattening of the hemostatic clip which is being applied at the same time (FIG. 15), and total collapse of the blood vessel to which the clip is applied. Also, the limited translation of the released hemostatic clip assures that only one clip may advance beyond the shoulder 79 during each actuation of the device.

Figures 17, 18:
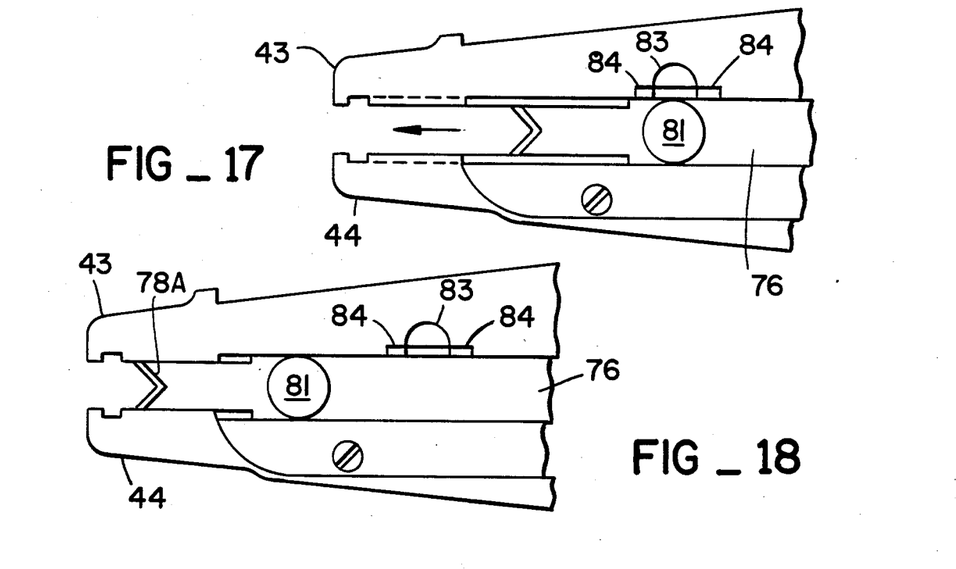
FIG. 17 is a side elevation of the jaw portion of the invention, shown with the jaws reopened fully and the clip releasing member in the retracted position.
FIG. 18 is a side elevation of the jaw portion of the invention, with the jaws fully open and the clip releasing member fully advanced.

As the trigger lever 46 is released following full closure of the jaws 43 and 44, the upper jaw assembly is rotated upwardly by the restoring force of spring 104 so that the notch 83 and camming surfaces 84 disengage the button 81. The shoulder 79 then resumes its blocking position in the window 74, and the upper jaw returns to its fully open position (FIG. 17). Further release of the trigger lever causes the trigger assembly to translate toward the distal end of the device under the urging of the spring 45. The V-shaped notch 78A in the distal end of the member 76 engages the portion 26 of the hemostatic clip just released, and pushes the clip distally toward the jaws 43 and 44. With the jaws fully opened, the grooves 73 formed therein are aligned with the passageway 57, so that the slide member 76 may push the released hemostatic clip distally into the grooves 73 of the jaws. Thus the completion of one hemostatic clip application disposes the device 25 to be ready to be used immediately for another application procedure. As the column of hemostatic clips within the passageway 57 advances toward the distal end and is individually dispensed and applied, the numerical indicia displayed in the window 71 of the device decrements by one digit to indicate the number of hemostatic clips remaining within the device.

Figure 22:
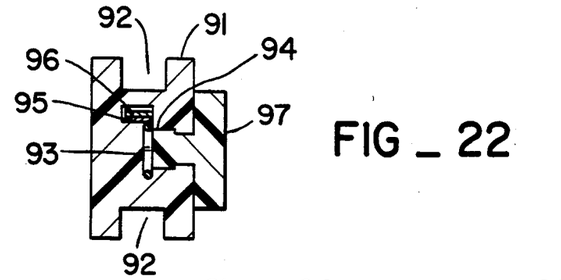
FIG. 22 is a cross-sectional view of the reloading magazine of the present invention.
Figure 23:
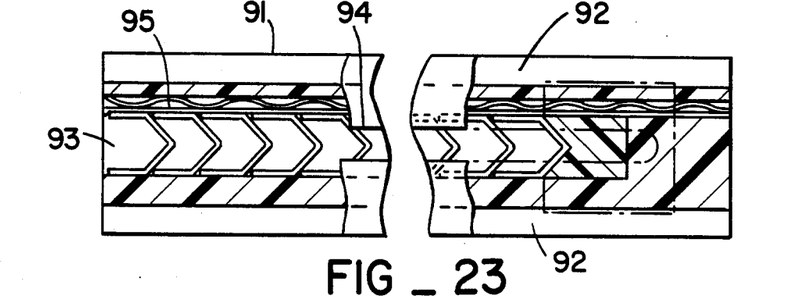
FIG. 23 is a plan view of the reloading magazine of the present invention.

A salient feature of the present invention is the provision of a reloading magazine system particularly adapted for the device. As shown in FIGS. 22 and 23, a loading magazine 91 is provided with a generally rectangular cross-section, and a pair of opposed grooves 92 extending longitudinally therealong. An internal passageway 93 extends longitudinally in the magazine 91, and communicates with a slot opening 94 which also extends the length of the magazine. As disclosed previously in the device 25, one side of the internal passageway 93 is formed by a movable blade wall backed by a leaf spring 96 having the configuration of a smooth periodic curve. The blade yields toward the spring 96 and prevents binding of the hemostatic clips 30 which are received in the passageway 93.

The magazine 91 includes a slide member 97 which is received in the slot 94 and extends inwardly into the passageway 93. The slide member 97 is provided to translate a column of hemostatic clips which are disposed within the passageway 93.

Figure 21:
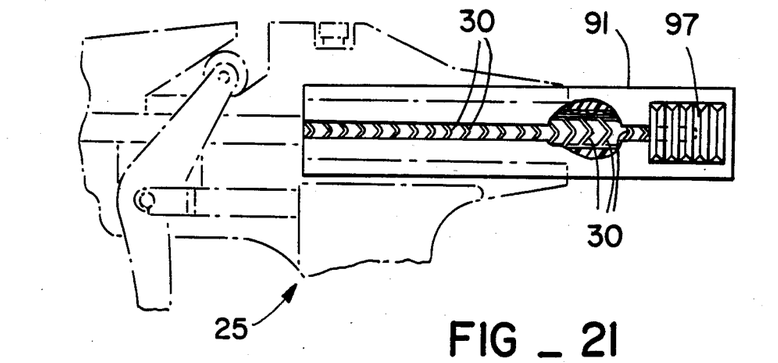
FIG. 21 is a partial cut-away view of the reloading magazine of the present invention.

As shown in FIG. 21, the magazine 91 is used by first loosening the detent screw assembly 72 and removing the tubular member 62 and the associated plunger 64 from the device 25. The magazine 91 is then introduced into the slot 56 with the longitudinal notches 92 of the magazine engaging the opposed sides of the slot 56. The magazine is fully inserted in the slot 56 so that the interior passageway 93 of the magazine is brought into abutting registration with the interior passageway 57 of the device 25. Thereafter, the slide member 97 is translated along the slot 94 to urge the column of hemostatic clips disposed in the passageway 93 to translate distally and transfer into the passageway 57 of the device 25. In this way, twenty or more hemostatic clips may be reloaded into the device 25 within a few seconds. The magazine 91 is then removed from the slot 56, and the plunger 64 and tubular member 62 are re-installed in the device 25.

It should be noted that there is a unique relationship among the springs 45, 63, and 104. It is necessary that the sum of the restoring forces applied to the pivot 52 by the springs 45 and 63 is less than the restoring force of the spring 104 acting on the same pivot. This condition assures that initial actuation of the trigger will cause initial translation of the trigger mechanism. If the sum of the restoring forces of the springs 45 and 63 is more than the force applied by the arm spring 104, the trigger assembly will initially rotate before translating, and the device will fail to operate properly.

It may be appreciated that the procedure involved in dispensing and applying a hemostatic clip using the present invention is extremely quick and easy to accomplish, using the manual force of one hand. Each dispensing and applying cycle rearms the device with a newly released clip which is ready to be applied in a subsequent hemostatic clip applying procedure. The rapidity with which the present invention may be employed in tying off blood vessels provides an important advance in surgical techniques. Likewise, the ability to reload the present invention quickly and easily with a full supply of hemostatic clips also minimizes wasted surgical time. It may be appreciated that the entire device can be autoclaved and sterilized for reuse. Furthermore, the strength of the construction of the present invention achieves a flattening of the hemostatic clips to within a few thousandths of an inch, far closer than any device known in the prior art

We claim:

1. A device for storing, dispensing, and applying hemostatic clips, comprising a longitudinally extending first member having a proximal end and a distal end; means for storing a plurality of hemostatic clips, comprising a passageway extending longitudinally in said first member and adapted to receive said plurality of hemostatic clips in column fashion; means for advancing said column of hemostatic clips toward said distal end of said first member; jaw means adjacent to said distal end of said first member for crimping and flattening each of said hemostatic clips, clip releasing means disposed adjacent to said distal end of said first member for releasing and advancing each of said hemostatic clips singularly and consecutively from said column in said passageway to said jaw means; manual lever means for actuating said jaw means and said clip releasing means, and means for preventing jamming of said hemostatic clips in said passageway, said last mentioned means including at least one wall defining said passageway, said wall being movable away from said hemostatic clips.

2. The device of claim 1, further including magazine reloading means for resupplying hemostatic clips to said passageway.

3. The device of claim 2, wherein said magazine means includes a magazine having a second plurality of hemostatic clips retained therein, and means for releasably securing said magazine to the proximal end of said passageway.

4. The device of claim 3, further including a guideway extending through said magazine, said second plurality of hemostatic clips being stored in said guideway in column fashion.

5. The device of claim 4, wherein one side of said guideway is defined by a movable blade wall backed by a leaf spring having the configuration of a smooth, periodic wave.

6. The device of claim 4, further including means for translating said second plurality of hemostatic clips from said guideway to said passageway in column order.

7. The device of claim 6, wherein said last mentioned means includes a slot opening in said magazine extending parallel to said guideway and opening thereto, and an ejection member translatably disposed in said slot opening and engaging said second plurality of hemostatic clips.

8. The device of claim 1, further including spring means for resiliently biasing said movable wall toward said hemostatic clips.

9. The device of claim 8, wherein said spring means includes a blade spring extending substantially the entire length of said movable wall and adapted to impinge thereon.

10. A device for storing and applying a plurality of hemostatic clips, comprising; a frame member extending longitudinally and having narrow lateral width, a handle extending downwardly from a proximal end of said frame member, a trigger assembly disposed adjacent to said handle, a fixed lower jaw extending from the distal end of said frame member, a first clevis member straddling an upper medial portion of said frame member and pivotally secured thereto, an upper jaw extending distally from said clevis member and positioned to be rotated by said clevis member into impingement with said lower jaw, said trigger assembly including a second clevis member straddling a medial portion of said frame member and a trigger lever extending downwardly from the lower end of said clevis member, a roller secured to the upper end of said clevis member, an oblique camming surface disposed at the proximal end of said first clevis member and adapted to be engaged by said roller, a passageway extending longitudinally through said frame member and having a distal end opening between said upper and lower jaws, said passageway being adapted to receive a plurality of hemostatic clips in column fashion, means for urging said plurality of hemostatic clips toward said distal end of said passageway, including a plunger received translatably in said passageway and compression spring means for urging said plunger toward said distal end of said passageway, a slide member translatably secured to the exterior of said frame member, means for joining the proximal end of said slide member to said second clevis member, an access window formed in the distal end of said passageway, a stop lug secured to the distal end of said slide member and disposed to extend through said window to said passageway to limit distal translation of said hemostatic clips in said passageway, button means extending outwardly from said slide member, and means secured to said upper jaw for engaging said button means and urging said button means, said slide member and said stop lug outwardly to release and advance a the distal one of said hemostatic clips as said upper jaw descends to impinge upon said lower jaw.

11. A device for storing, dispensing, and applying hemostatic clips, comprising a longitudinally extending first member having a proximal end and a distal end; means for storing a plurality of hemostatic clips, comprising a passageway extending longitudinally in said first member and adapted to receive said plurality of hemostatic clips in column fashion; means for advancing said column of hemostatic clips toward said distal end of said first member, including plunger means extending into said passageway and disposed to drive said column of hemostatic clips distally; jaw means adjacent to said distal end of said first member for closing and flattening each of said hemostatic clips, clip releasing means disposed adjacent to said distal end of said first member for releasing and advancing each of said hemostatic clips singularly and consecutively from said column in said passageway to said jaw means, said clip releasing means including a slide member secured to said first member and adapted for longitudinal translation therealong; trigger lever means joined to said slide member to drive said slide member to retract proximally and return distally, stop lug means extending from said slide member and adapted to engage the most distal one of said column of said hemostatic clips and to drive said column proximally as said slide member is retracted, and cam means joined to said jaw means for disengaging said stop lug means from said most distal one of said hemostatic clips to permit the latter to advance past said stop lug means as said jaw means are closed.

12. The device of claim 11, wherein said means for advancing said column of hemostatic clips includes a plunger translatably and removably disposed in said passageway, and means for urging said plunger toward said distal end of said first member.

13. The device of claim 12, wherein said last mentioned means includes a hollow tubular member removably secured to said proximal end of said first member, first compression spring means disposed in said tubular member, said plunger being translatably secured at one end within said tubular member and impinging on said first compression spring means.

14. The device of claim 13, wherein said first member includes a slot cutout formed in the proximal end thereof and communicating with the proximal end of said passageway, said tubular member being removably secured in said slot cutout.

15. The device of claim 12, further including means for indicating the number of hemostatic clips retained in said passageway.

16. The device of claim 15, wherein said last mentioned means includes a display window extending from the exterior of said first member to said passageway.

17. The device of claim 16, further including serial numerical indicia formed on said plunger and disposed to decrement past said window as said column of hemostatic clips advances incrementally along said passageway.

18. The device of claim 11, further including clip advancing means extending from the distal end of said slide member and disposed to drive the advanced, most distal one of said hemostatic clips to the distal end of said jaw means as said slide member returns distally.

19. The device of claim 18, wherein said clip advancing means includes a notch formed in the distal end of said slide member and disposed to engage the bail portion of said advanced, most distal one of said hemostatic clips.

20. The device of claim 11, wherein said trigger lever means includes a trigger lever, and a pivot pin extending through a medial portion of said trigger lever and through said slide member to join said trigger lever to said slide member in pivotting fashion.

21. The device of claim 20, further including a second member pivotally secured to said first member, said jaw means including a pair of jaws disposed at the distal ends of said first and second members in opposed fashion, said jaws being closable by rotation of said second member.

22. The device of claim 21, further including a camming surface disposed on the proximal end of said second member, said trigger lever including a cam roller follower disposed to engage said camming surface and adapted to rotate said second member to close said jaws as said trigger lever is rotated.

23. The device of claim 22, further including a closed slot extending through said first member, said pivot pin extending through said closed slot in translatable fashion, said trigger lever being actuable to translate said pivot pin and slide member proximally to the limit of said closed slot and thereafter to rotate about said pivot pin to effect closure of said jaws.

24. A device for storing, dispensing, and applying hemostatic clips, comprising a longitudinally extending first member having a proximal end and a distal end; means for storing a plurality of hemostatic clips, comprising a passageway extending longitudinally in said first member and adapted to receive said plurality of hemostatic clips in column fashion; means for advancing said column of hemostatic clips toward said distal end of said first member; a pair of jaws adjacent to said distal end of said first member for crimping and flattening each of said hemostatic clips, clip releasing means disposed adjacent to said distal end of said first member for releasing and advancing each of said hemostatic clips singularly and consecutively from said column in said passageway to said jaws, a second member pivotally joined to said first member, one of said jaws being joined to the distal end of said second member and disposed in opposition to the other jaw, a trigger lever pivotally joined to said first member, a cam follower extending from a distal end portion of said trigger lever, a cam surface disposed on a proximal portion of said second member, said cam follower being disposed to rotate said second member to close said jaws as said trigger lever is rotated.

25. The device of claim 23, further including a pair of parallel, longitudinally extending grooves formed in the confronting surfaces of said pair of jaws, said grooves being configured to receive and retain the opposed leg portions of a hemostatic clip.

26. The device of claim 24, wherein said second member includes a clevis portion straddling a medial portion of said first member, said cam surface being disposed at the proximal end of said clevis portion.

27. A device for storing, dispensing, and applying hemostatic clips, comprising a longitudinally extending first member having a proximal end and a distal end; means for storing a plurality of hemostatic clips, comprising a passageway extending longitudinally in said first member and adapted to receive said plurality of hemostatic clips in column fashion; means for advancing said column of hemostatic clips toward said distal end of said first member; jaw means adjacent to said distal end of said first member for crimping and flattening each of said hemostatic clips, clip releasing means disposed adjacent to said distal end of said first member for releasing and advancing each of said hemostatic clips singularly and consecutively from said column in said passageway to said jaw means; manual lever means for actuating said jaw means and said clip releasing means, said means for advancing said column of hemostatic clips including a plunger translatably and removably disposed in said passageway, means for urging said plunger toward said distal end of said first member, means for indicating the number of hemostatic clips retained in said passageway, including a display window extending from the exterior of said first member to said passageway, serial numerical indicia formed on said plunger and disposed to decrement past said window as said column of hemostatic clips advances incrementally along said passageway, said clip releasing means including a slide member, means for joining said slide member to said first member for longitudinal translation therealong, means for joining the proximal end of said slide member to said manual lever means for reciprocal translation therewith, an access window extending from the exterior of said first member to said passageway at the distal end thereof, stop lug means disposed at the distal end of said slide member and projecting through said access window into said passageway to engage and limit distal translation of the most distal one of said hemostatic clips in said passageway, means for urging said stop lug laterally outwardly to disengage and pass said most distal hemostatic clip to said jaw means, said jaw means including one movable jaw, and said last mentioned means includes a camming surface disposed on said movable jaw, and button means extending outwardly from said slide member and adapted to engage said camming means during actuation of said movable jaw.

28. A device for storing, dispensing and applying hemostatic clips, comprising a longitudinally extending first member having a proximal end and a distal end; means for storing a plurality of hemostatic clips, comprising a passageway extending longitudinally in said first member and adapted to receive said plurality of hemostatic clips in column fashion; means for advancing said column of hemostatic clips toward said distal end of said first member; jaw means adjacent to said distal end of said first member for crimping and flattening each of said hemostatic clips, clip releasing means disposed adjacent to said distal end of said first member for releasing and advancing each of said hemostatic clips singularly and consecutively from said column in said passageway to said jaw means; manual lever means for actuating said jaw means and said clip releasing means, a first jaw extending fixedly from said distal end of said first member, a second member pivotally secured to said first member at a first pivot axis, a second jaw extending from said second member in spaced apart opposition to said first jaw and adapted to be rotated into impingement with said first jaw, said second member including a clevis portion straddling a distal and medial portion of said first member, said manual lever means including a trigger assembly extending from a medial portion of said first member, said trigger assembly including a trigger clevis portion straddling a medial portion of said first member and pivotally secured thereto, a trigger lever extending from said trigger clevis portion, a closed slot extending longitudinally in said first member adjacent to said trigger assembly, a pivot pin extending through said slot and through said trigger clevis portion, said pin being translatably disposed in said slot, said trigger clevis portion being pivotable about said pin, first compression spring means associated with said means for advancing said column of hemostatic clips, second compression spring means acting on said pin and opposing proximal translation thereof, and third spring means associated with said second member to oppose rotation of said second jaw into impingement with said first jaw, the sum of the restoring forces of said first and second spring means being less than the restoring force of said third spring means.

* * * * *